US010451561B2

(12) United States Patent
Oota et al.

(10) Patent No.: US 10,451,561 B2
(45) Date of Patent: Oct. 22, 2019

(54) INSPECTION SYSTEM (71) Applicant: FANUC CORPORATION, Yamanashi (JP)

(72) Inventors: Yuusuke Oota, Yamanashi (JP); Fumikazu Warashina, Yamanashi (JP)

(73) Assignee: FANUC CORPORATION, Yamanashi (JP)

(*) Notice: Subject to any disclaimer, the term of this patent is extended or adjusted under 35 U.S.C. 154(b) by 0 days.

(21) Appl. No.: 16/127,824

(22) Filed: Sep. 11, 2018

(65) Prior Publication Data
US 2019/0120771 A1 Apr. 25, 2019

(30) Foreign Application Priority Data

Oct. 25, 2017 (JP) ................. 2017-206144

(51) Int. Cl.
G01N 1/34 (2006.01)
G01N 21/88 (2006.01)
G01N 21/15 (2006.01)
G05B 19/418 (2006.01)
G01N 21/95 (2006.01)

(52) U.S. Cl.
CPC .......... *G01N 21/8851* (2013.01); *G01N 1/34* (2013.01); *G01N 21/15* (2013.01); *G01N 21/9515* (2013.01); *G05B 19/4183* (2013.01); *G01N 2021/151* (2013.01); *G01N 2021/8887* (2013.01); *G01N 2021/9518* (2013.01); *G05B 2219/40562* (2013.01)

(58) Field of Classification Search
CPC ...... G01N 21/8851; G01N 1/34; G01N 21/15; G01N 21/9515; G05B 19/4183

USPC ....................................... 356/237.2
See application file for complete search history.

(56) References Cited

U.S. PATENT DOCUMENTS

2003/0147725 A1* 8/2003 Glass .................. B01D 21/245
414/8
2016/0121444 A1* 5/2016 Matsuno .............. B23Q 11/006
409/131
2017/0122871 A1 5/2017 Meer
(Continued)

FOREIGN PATENT DOCUMENTS

JP 4-52508 2/1992
JP 6-82387 3/1994
JP 2002-372498 12/2002
(Continued)

Primary Examiner — Roy M Punnoose
(74) Attorney, Agent, or Firm — Wenderoth, Lind & Ponack, L.L.P.

(57) ABSTRACT

An inspection system makes image inspection on an inspection target. The inspection system includes: an image capture device that captures an image of the inspection target; a blower with a blow nozzle from which clean gas is blown out to the inspection target; a robot with an arm tip to which the image capture device and the blow nozzle, or the inspection target is attached; and as inspection device that makes image inspection on the inspection target based on an image captured by the image capture device. The inspection device generates an operation program for a robot based on the position of the image capture device and that of the blow nozzle relative to each other so as to move the blow nozzle ahead of the image capture device relative to the inspection target.

8 Claims, 12 Drawing Sheets (56) References Cited

U.S. PATENT DOCUMENTS

2018/0276933 A1* 9/2018 Nakanishi ............ B65G 47/493

FOREIGN PATENT DOCUMENTS

| JP | 2004-108956 | 4/2004 |
| JP | 2005-121599 | 5/2005 |
| JP | 2015-141096 | 8/2015 |

* cited by examiner

INSPECTION SYSTEM

This application is based on and claims the benefit of priority from Japanese Patent Application No. 2017-206144, filed on 25 Oct., 2017, the content of which is incorporated herein by reference.

BACKGROUND OF THE INVENTION

Field of the Invention

The present invention relates to an inspection system that inspects an inspection target based on an image of the inspection target captured by an image capture device.

Related Art

Patent Document 1 describes as inspection system that inspects an inspection target for a defect (flaw, for example) on a surface of the inspection target, for example, based on an image of the inspection target captured by an image capture device. In this inspection system, the position of the image capture device relative to the inspection target is controlled by attaching the image capture device to the tip of an arm of a robot and controlling the robot.

In such an inspection system using an image captured by the image capture device, if dust or dirt in the air adheres to an inspection surface of the inspection target, such an adhering object may be detected erroneously as a defect (flaw). In another case, if a cutting fluid or a cleaning fluid having been used in a previous step adheres to the inspection surface of the inspection target, appearance in an image may be changed by a difference of the light reflectivity of the cutting fluid or the cleaning fluid from the light reflectivity of the surface of the inspection target. In this case, such an adhering object may be detected erroneously as a defect (flaw), or the presence of such an adhering object may cause overlooking of a defect (flaw) that is originally intended to be detected.

In this regard, in an inspection system described in Patent Document 2 that makes inspection to determine the presence or absence of a defect (flaw, for example) on a surface of an inspection target based on an image of the inspection target captured by an image capture device, an air nozzle for jetting of air is provided in front of the image capture device in a traveling direction of the image capture device. By doing so, a foreign object adhering to the surface of the inspection target is removed.

Patent Document 1: Japanese Unexamined Patent Application, Publication No. 2005-121599
Patent Document 2: Japanese Unexamined Patent Application, Publication No. 2004-108956

SUMMARY OF THE INVENTION

The present invention is intended to provide an inspection system that reduces the likelihood of erroneous detection or overlooking of a defect caused by an object adhering to a surface of an inspection target.

(1) An inspection system according to the present invention (inspection system 1 described later, for example) makes image inspection on an inspection target (workpiece W described later, for example). The inspection system includes: an image capture device (camera 10 described later, for example) that captures an image of the inspection target; a blower (blower 20 described later, for example) with a blow nozzle (blow nozzle 22 described later, for example) from which clean gas is blown out to the inspection target; a robot (robot 30 described later, for example) with an arm tip (arm tip 32 described later, for example) to which the image capture device and the blow nozzle, or the inspection target is attached; and an inspection device (inspection device 50 described later, for example) that makes image inspection on the inspection target based on an image captured by the image capture device. The inspection device generates an operation program for the robot based on the position of the image capture device and that of the blow nozzle relative to each other so as to move the blow nozzle ahead of the image capture device relative to the inspection target.

(2) In the inspection system described in (1), the image capture device and the blow nozzle may be attached to the arm tip of the robot, and the inspection device may generate the operation program for the robot so as to achieve agreement between a direction from the image capture device toward the blow nozzle and an inspection direction of an inspection path for image inspection on the inspection target.

(3) In the inspection system described in (2), the inspection device may set the direction from the image capture device toward the blow nozzle as a traveling direction (X direction) of the arm tip of the robot, and the inspection device may generate the operation program for the robot so as to achieve agreement between the traveling direct on of the arm tip of the robot and the inspection direction of the inspection path for image inspection on the inspection target.

(4) in the inspection system described in any one of (1) to (3), the inspection device may generate the operation program for the robot based on teaching of the operation of the robot by an inspector.

(5) In the inspection system described in any one of (1) to (3), the inspection device may generate the operation program for the robot automatically based on a direction from the image capture device toward the blow nozzle or a direction opposite the direction from the image capture device toward the blow nozzle, and an inspection direction of an inspection path from a current position to a next inspection point.

(6) In the inspection system described in any one of (1) to (5), the inspection device may generate an inspection path for image inspection on the inspection target automatically by setting multiple inspection points on an inspection surface of the inspection target and determining the order in which inspection is made at the multiple inspection points.

(7) in the inspection system described in any one of (1) to (6), a blowing-out direction of the clean gas from the blow nozzle may be tilted to a direction from the image capture device toward the blow nozzle.

(8) In the inspection system described in (7), the blowing-out direction of the clean gas from the blow nozzle may further be tilted to a direction intersecting the direction from the image capture device toward the blow nozzle.

The present invention is capable of providing an inspection system that reduces the likelihood of erroneous detection or overlooking of a defect caused by an object adhering to a surface of an inspection target.

DETAILED DESCRIPTION OF THE INVENTION

Exemplary embodiments of the present invention will be described below by referring to the accompanying drawings. A part in one drawing and a part in a different drawing equal to or corresponding to each other will be given. the same sign.

First Embodiment

Figure 1:
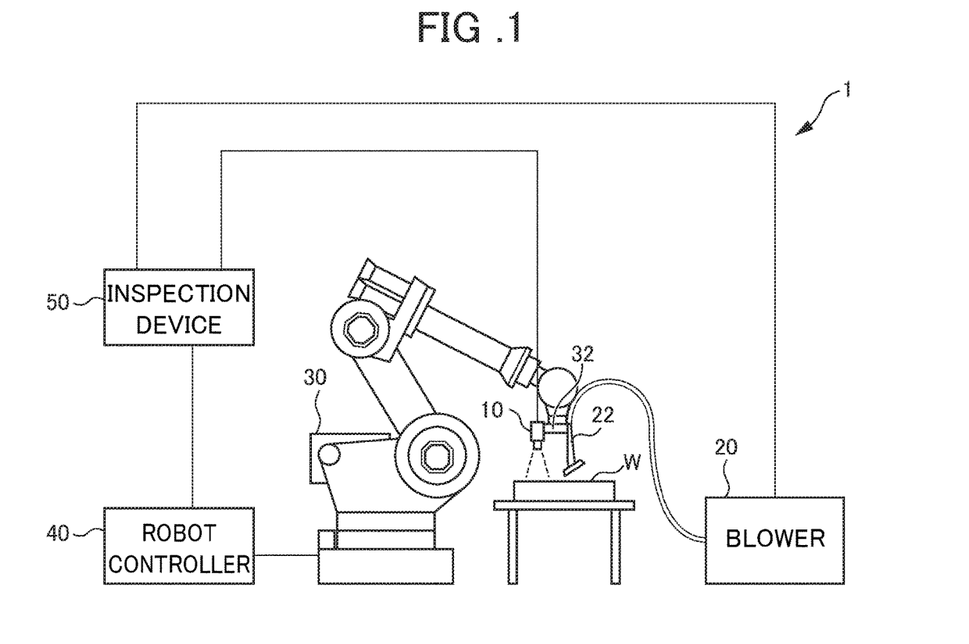
FIG. 1 shows the configuration of an inspection system according to an embodiment.

FIG. 1 shows the configuration of an inspection system according to a first embodiment. An inspection system 1 shown in FIG. 1 is a system that makes inspection to determine the presence or absence of a defect (flaw, for example) on a surface (inspection surface) of a workpiece (inspection target) W, for example, based an image of the workpiece W captured by a camera (image capture device) 10. The inspection system 1 includes the camera (image capture device) 10, a blower 20, a robot 30, a robot controller 10, and an inspection device 50.

The camera 10 captures an image of the workpiece W under control by the inspection device 50. The camera 10 provides the inspection device 50 with the captured image of the workpiece W. The blower 20 blows out clean gas from a blow nozzle 22 under control by the inspection device 50. The clean gas to be used may be air, nitrogen gas, or carbon dioxide gas, for example. In the following description, air is used as an example of the clean gas.

Figure 2:
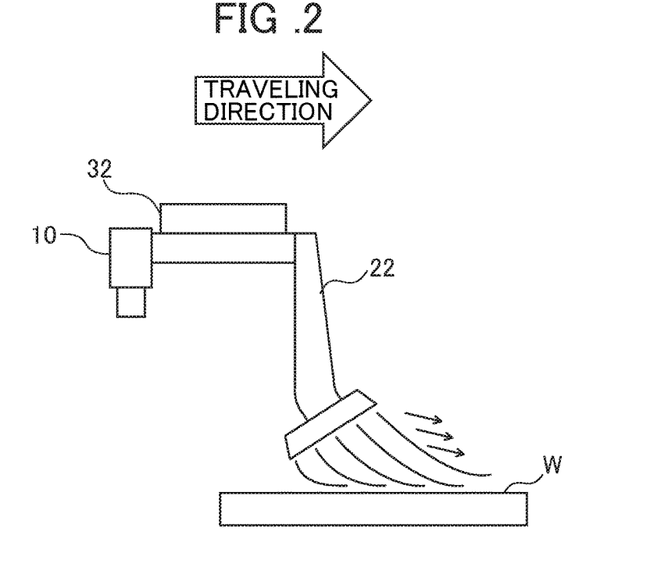
FIG. 2 is a side view of an arm tip of a robot shown in FIG. 1.

A publicly-known robot manipulator is available as the robot 30. A manipulator having six joint axes is illustrated. as the robot 30 in FIG. 1. The robot 30 has an arm tip 32 to which the camera 10 and the blow nozzle 22 of the blower 20 are attached. FIG. 2 is a side view of the arm tip 32 of the robot 30. As shown in FIG. 2, the camera 10 is attached to one side of the arm tip 32 so as to capture an image of the workpiece W arranged below the camera 10. The blow nozzle 22 is attached to the opposite side of the arm tip 32 so as to blow out air to the workpiece W arranged below the blow nozzle 22. The blow nozzle 22 is formed or arranged in such a manner that a blowing-out direction of air is tilted to a direction from the camera 10 toward the blow nozzle 22 (a traveling direction of the arm tip 32 of the robot 30 described later).

The robot controller 40 executes an operation program for a robot provided from the inspection device 50 to control the position and the posture of the arm tip 32 of the robot 30 so as to move the camera 10 and the blow nozzle 22 relative to the workpiece W.

The inspection device 50 executes an inspection program to make inspection to determine the presence or absence of a defect on the surface (inspection surface) of the workpiece W based on an image of the workpiece W captured. by the camera 10. The inspection device 50 generates an operation program for a robot so as to move the blow nozzle 22 ahead of the camera 10 relative to the workpiece W based on the position of the camera 10 and that of the blow nozzle 22 relative to each other. In this embodiment, the inspection device 50 generates the operation program for a robot based on teaching of the operation of the robot 30 by an inspector. This will be described in detail below.

Figure 3:
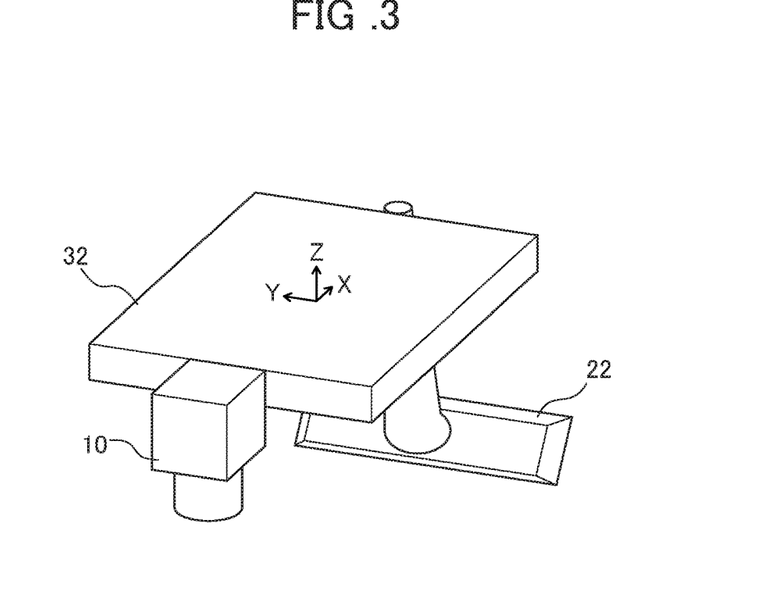
FIG. 3 is a perspective view of the arm tip of the robot shown in FIG. 1.

FIG. 3 is a perspective view of the arm tip 32 of the robot 30. As shown in FIG. 3, the inspection device 50 sets a coordinate system at the position of the arm tip 32 of the robot 30 for determining the position and the posture of the arm tip 32. Regarding this setting, the inspection device 50 sets an X-axis direction as the direction from the camera 10 toward the blow nozzle 22 (a direction in which a blowing-out direction of air tilts). Further, the inspection device 50 sets the X-axis direction as a traveling direction of the arm tip 32 of the robot 30 during inspection. In this way, the direction from the camera 10 toward the blow nozzle 22 is set as the traveling direction of the arm tip 32 of the robot 30 during inspection. The coordinate system for determining the position and the posture of the robot 30 may be set at the position of the camera 10 or at the position of the blow nozzle 22, instead of the position of the arm tip 32. The direction of each axis in the coordinate system for determining the position and the posture of the robot 30 may be set freely. In this case, the inspection device 50 also sets the direction from the camera 10 toward the blow nozzle 22 as the traveling direction of the arm tip 32 of the robot 30 during inspection.

Figure 4:
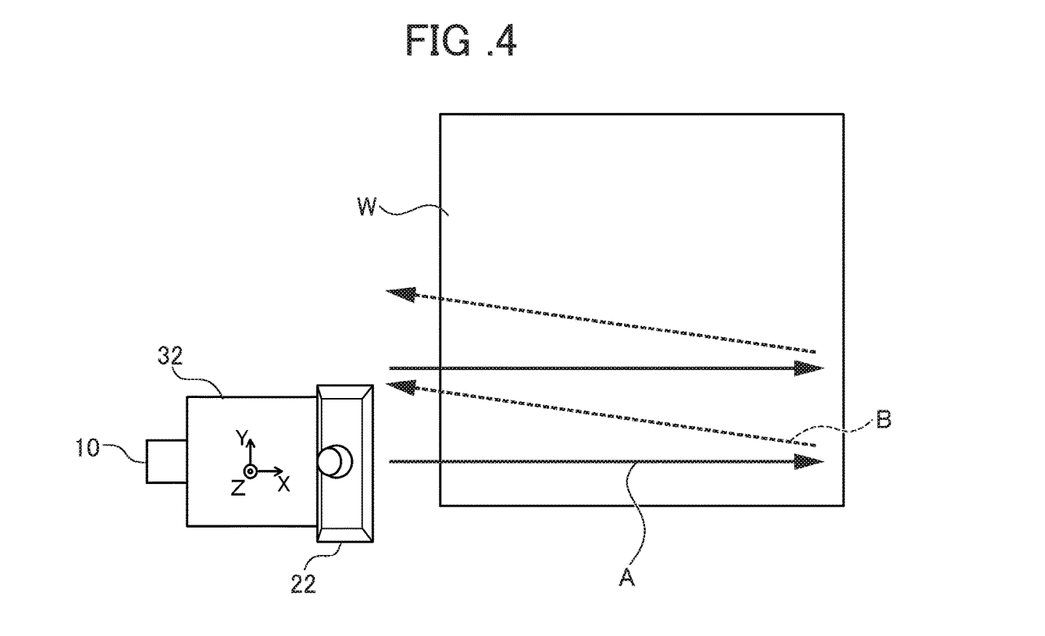
FIG. 4 is a plan view of the arm tip of the robot and a workpiece for explaining an example of teaching of the operation of the robot by an inspector.

The inspection device 50 generates the operation program for a robot so as to achieve agreement between the X-axis direction, specifically, between the direction from the camera 10 toward the blow nozzle 22 and an inspection direction of an inspection path for image inspection on the workpiece W. In this embodiment, the inspection device 50 generates the operation program for a robot based on teaching of the operation of the robot by an inspector. FIG. 4 is a plan view of the arm 32 of the robot 30 and the workpiece W for explaining an example of teaching of the operation of the robot by the inspector. As shown in FIG. 4, the inspector teaches an inspection path and an inspection direction so as to capture images of the entire inspection surface of the workpiece W. For example, the inspector moves the arm tip 32 only in the +X direction (A direction) to teach the position of the camera 10 at the arm tip 32 at each inspection point from one end (closer to the −X direction.) to the opposite end (closer to the +X direction) of the inspection surface of the workpiece W. This teaching is repeated by making a shift in the Y direction (B direction). The inspection device 50 may generate the operation program for a robot based on this teaching.

Figure 5A:
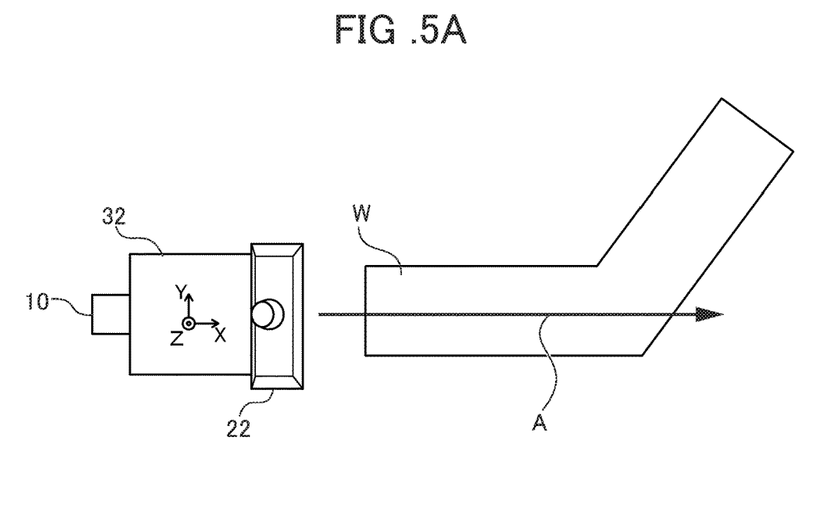
FIG. 5A is a plan view of the arm tip of the robot and the workpiece for explaining a different example of teaching of the operation of the robot by an inspector.
Figure 5B:
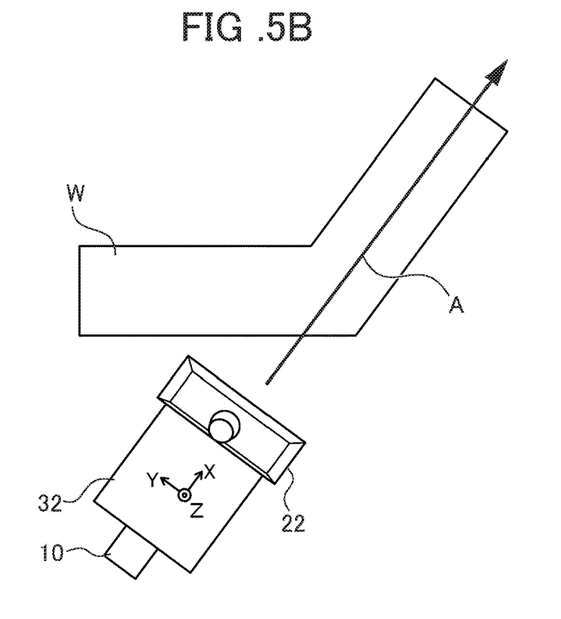
FIG. 5B is a plan. view of the arm tip of the robot and the workpiece for explaining the different example of teaching of the operation of the robot by the inspector.

As long as the blow nozzle 22 is ahead of the camera 10 in a traveling direction, an inspection path and an inspection direction may be determined freely. For example, as shown in FIGS. 5A and 5B, an inspection path and an inspection direction may be determined so as to change a traveling direction by rotating the arm tip 32 around the Z axis. If the posture of the arm tip 32 (camera 10) is changed for inspection on a different surface of the workpiece W, the blow nozzle 22 can also be located ahead of the camera 10 during the inspection by teaching an inspection path so as to move the arm tip 32 only in the +X direction, specifically, in the direction from the camera 10 toward the blow nozzle 22.

The blower 20 may blow out air from the blow nozzle 22 constantly during image inspection on the workpiece W, or may blow out air only when the arm tip 32 of the robot 30 travels in an inspection direction.

As described above, in the inspection system 1 of this embodiment, the inspection device 50 generates an operation program for a robot based on the position of the camera 10 and that of the blow nozzle 22 relative to each other so as to achieve agreement between. the direction from the camera 10 toward the blow nozzle 22 and an inspection direction of an inspection path for image inspection on. the workpiece W, specifically, so as to move the blow nozzle 22 ahead of the camera 10 relative to the workpiece W. By doing so, the blow nozzle 22 first passes through a position for image capture by the camera 10 and blows out air to a viewing field of the camera 10 immediately before the image capture. This allows removal of an object adhering to a surface of the workpiece W within the viewing field of the camera 10 such as dust, dirt, a cutting fluid, or a cleaning fluid. This makes it possible to reduce the likelihood of erroneous detection or overlooking of a defect caused by an object adhering to the surface of the workpiece W to increase the rate of success of the inspection. An object in the air such as dirt may also adhere to the workpiece W during inspection. In this regard, in the inspection system 1 of this embodiment, air is blown out to the viewing field of the camera 10 immediately before image capture, so that an object adhering to the workpiece W during inspection can be removed also immediately before the image capture.

In the inspection system 1 of this embodiment, the blow nozzle 22 is formed or arranged in such a manner that a blowing-out direction of air is tilted to the direction from the camera 10 toward the blow nozzle 22 (a traveling direction of the arm tip 32 of the robot 30). This allows an object adhering to a surface (inspection surface) of the workpiece W to fly forward, thereby reducing the likelihood of flying of a foreign object with air toward the camera 10.

(Modification of First Embodiment: Modification of Blow Nozzle)

Figure 6A:
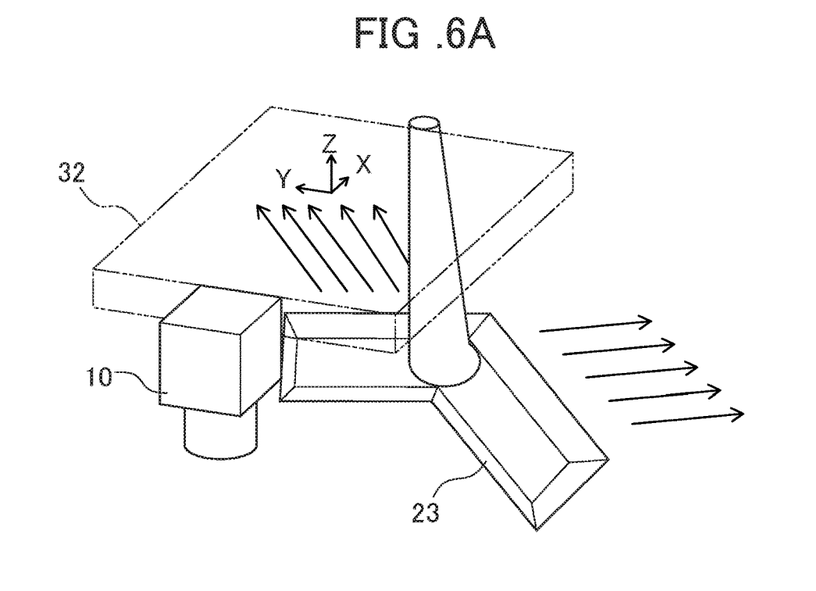
FIG. 6A is a perspective view of the arm. tip of the robot showing a blow nozzle according to a modification.
Figure 6B:
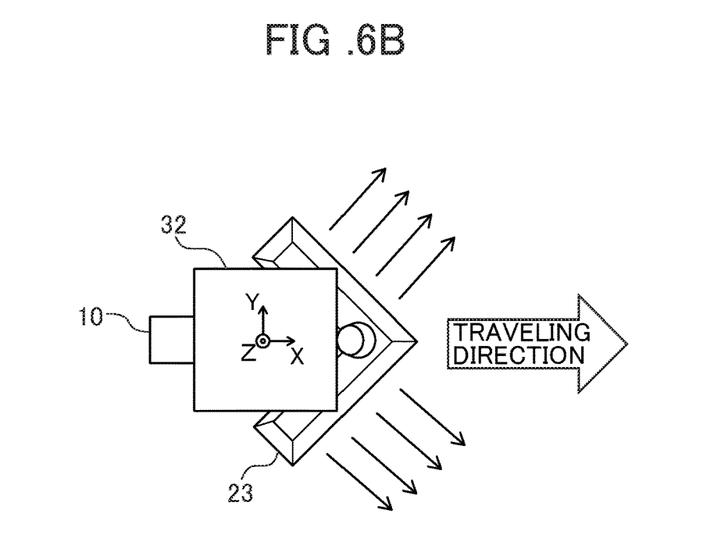
FIG. 6B is a plan view of the arm tip of the robot showing the blow nozzle according to the modification.

FIG. 6A is a perspective view of the arm tip 32 of the robot 30 showing a blow nozzle according to a modification. FIG. 6B is a plan view of the arm tip 32 of the robot 30 showing the blow nozzle according to the modification. As shown in FIGS. 6A and 6B, a blow nozzle 23 of the modification may be used instead of the blow nozzle 22. The blow nozzle 23 is also attached to the opposite side of the arm tip 32 so as to blow out air toward. the workpiece W arranged below the blow nozzle 23. The blow nozzle 23 is formed or arranged in such a manner that a blowing-out direction of air is tilted to a direction from the camera. 10 toward the blow nozzle 23 (a traveling direction of the arm tip 32 of the robot 30). The blow nozzle 23 is formed or arranged in a V-shaped pattern. in such a manner that a blowing-out direction of air is further tilted to both side directions intersecting the direction from the camera 10 toward the blow nozzle 23. Alternatively, the blow nozzle 23 may be formed or arranged in such a manner that a blowing-out direction of air is tilted only to one of both side directions. By doing so, an object adhering to a surface (inspection surface) of the workpiece W is allowed to fly forward from both sides, thereby reducing the likelihood of flying of a foreign object with air toward the camera.

In this embodiment, the workpiece W is installed fixedly, and the camera 10 and the blow nozzle 22 or 23 of the blower 20 are attached to the arm tip 32 of the robot 30, thereby moving the camera 10 and the blow nozzle 22 or 23 relative to the workplace W. Alternatively, the camera 10 and the blow nozzle 22 or 23 of the blower 20 may be moved relative to the workpiece W by fixedly installing the camera 10 and the blow nozzle 22 or 23, and gripping the workpiece W with the arm tip 32 of the robot 30. In this case, the inspection device 50 may set a direction opposite the direction from the camera 10 toward the blow nozzle 22 or 23 as a traveling direction of the workpiece W, and generate an operation program for a robot so as to achieve agreement between the set traveling direction of the workpiece W and an inspection direction of an inspection path for image inspection on the workpiece W. This moves the blow nozzle 22 or 23 ahead of the camera 10 relative to the workpiece W.

Second Embodiment

In the first embodiment, an operation program for a robot is generated based on teaching of the operation of the robot by an inspector. In a second embodiment, the operation program for a robot is generated automatically.

The configuration of an inspection system 1 of the second embodiment is the same as that of the inspection system 1 of the first embodiment shown in FIG. 1. The inspection system 1 of the second embodiment differs from the inspection system 1 of the first embodiment in the function and the operation of the inspection device 50.

When the inspection device 50 is taught the positions of a robot at all inspection points by an inspector to determine the order of passing through the inspection points, specifically, to determine an inspection path and an inspection direction, the inspection device 50 generates an operation program for a robot automatically so as to move the blow nozzle 22 ahead of the camera 10 relative to the workpiece W. This will be described In detail below.

Figure 7:
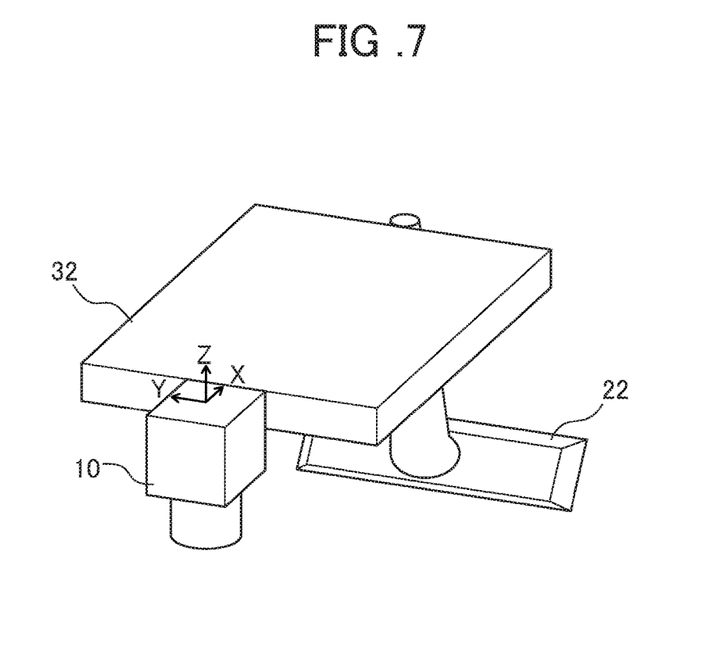
FIG. 7 is a perspective view of an arm tip of a robot in an inspection system according to a second embodiment.

FIG. 7 is a perspective view of the arm tip 32 of the robot 30. As shown in FIG. 7, the inspection device 50 sets a coordinate system at the position of the camera 10 for determining the position and the posture of the arm tip 32 of the robot 30. Regarding this setting, the inspection device 50 sets an X-axis direction as a direction from the camera 10 toward the blow nozzle 22 (a direction in which a blowing-out direction of air tilts). Further, the inspection device 50 sets the X-axis direction as a traveling direction of the arm tip 32 of the robot 30 during inspection. In this way, the direction from the camera 10 toward the blow nozzle 22 is set as the traveling direction of the arm tip 32 of the robot 30 during inspection.

Figure 8A:
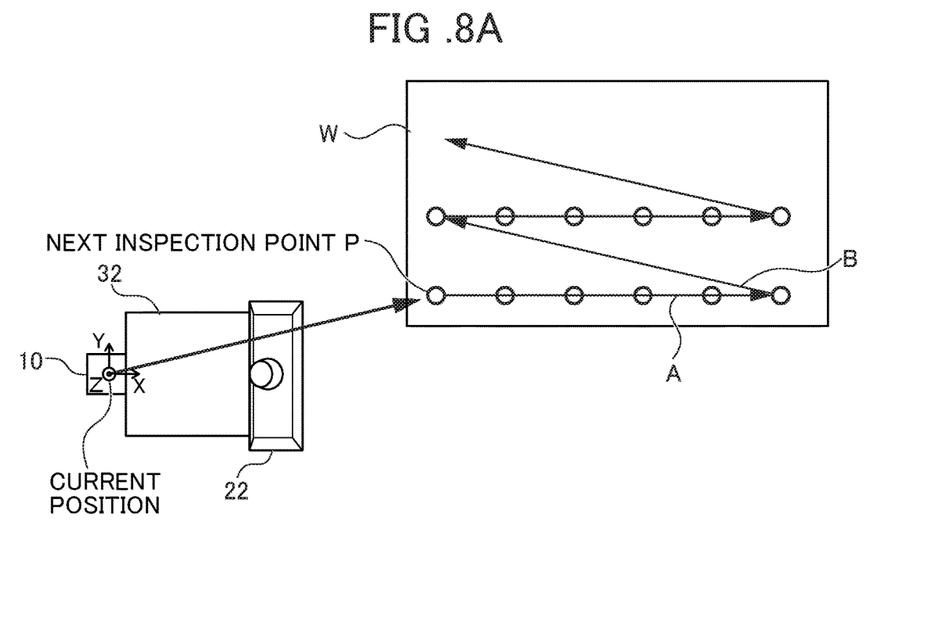
FIG. 8A is a plan view of the arm tip of the robot and a workpiece for explaining an. example of automatic generation of an operation program for a robot by an inspection device in the inspection system according to the second embodiment.
Figure 8B:
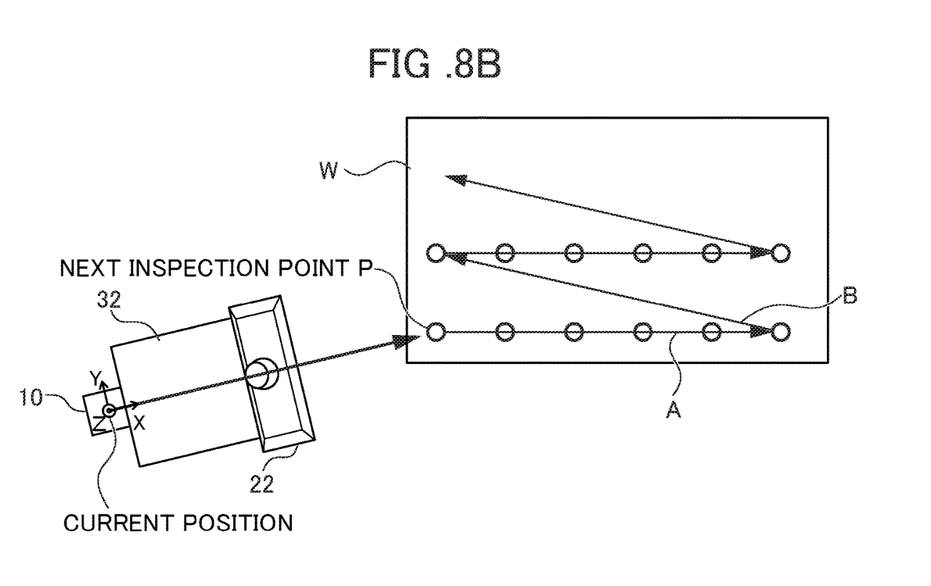
FIG. 8B is a plan view of the arm tip of the robot and the workpiece for explaining the example of automatic generation of the operation program for a robot by the inspection device in the inspection system according to the second embodiment.
Figure 8C:
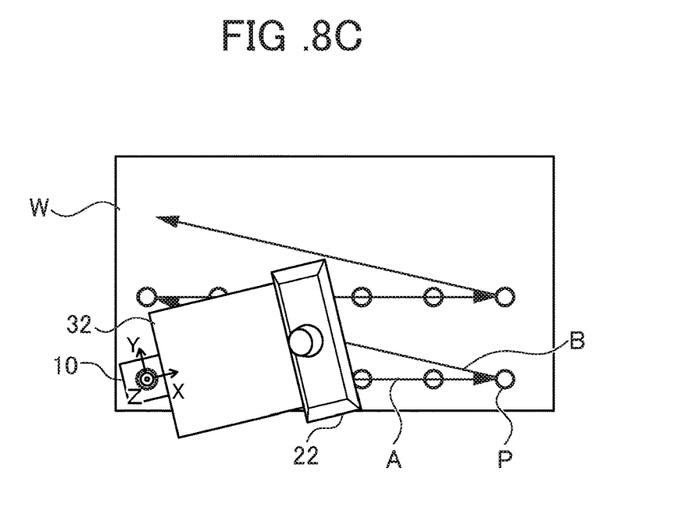
FIG. 8C is a plan view of the arm tip of the robot and the workpiece for explaining the example of automatic generation of the operation program for a robot by the inspection device in the inspection system according to the second embodiment.

The inspection device 50 generates the operation program for a robot so as to achieve agreement between the X-axis direction, specifically, between the direction from the camera 10 toward the blow nozzle 22 and an inspection direction of an inspection path for image inspection on the workpiece W. In this embodiment, the inspection device 50 generates the operation program for a robot automatically. FIGS. 8A to 8D are plan views of the arm tip 32 of the robot 30 and the workpiece W for explaining an example of automatic generation of the operation program for a robot. As shown in FIG. 8A, the inspection device 50 determines an inspection direction of an inspection path from a current position to a next inspection point. Next, as shown in FIG. 8B, the inspection device 50 generates the operation program for a robot automatically so as to achieve agreement between the X-axis direction, specifically, between the direction from the camera 10 toward the blow nozzle 22 and the inspection direction of the inspection path. By following this operation program, the robot controller 40 compensates for the direction and the posture of the arm tip 32 of the robot 30. Then, as shown in FIG. 8C, the arm tip 32 of the robot 30 is moved to a next inspection point.

Figure 8D:
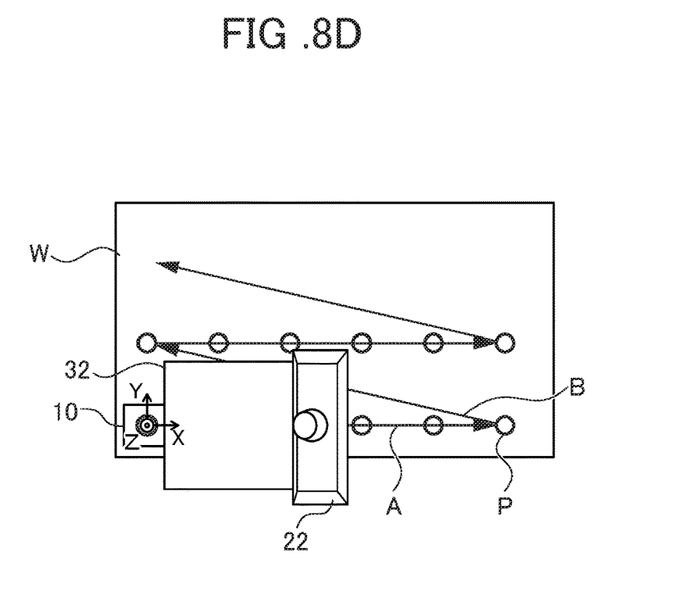
FIG. 8D is a plan view of the arm tip of the robot and the workpiece for explaining the example of automatic generation of the operation program for a robot by the inspection device in the inspection system according to the second embodiment.

Next, as shown in FIG. 8D, the inspection device 50 generates the operation program for a robot automatically so as to achieve agreement between the X-axis direction, specifically, between the direction from the camera 10 toward the blow nozzle 22 and the inspection direction of the inspection path. By following this operation program, the robot controller 40 compensates for the direction and the posture of the arm tip 32 of the robot 30. At this time, the inspection device 50 makes the camera 10 capture an image of the workpiece W by following the inspection program. The image of the workpiece W may be captured while the robot continues operating or while the robot is stopped for a moment.

The inspection device 50 performs the operations in FIGS. 8A to 8D repeatedly on all inspection points P (inspection paths A and B) on the workpiece W thereby generating the operation program for a robot automatically.

The inspection system 1 of this embodiment is capable of achieving an effect comparable to the effect achieved by the inspection system 1 of the first embodiment.

Third Embodiment

In the second embodiment, an inspection path for image inspection on the workpiece W is generated based on teaching by an inspector, and an operation program for a robot is generated automatically. In a third embodiment, an inspection path for image inspection on the workpiece W is also generated automatically.

The configuration of an inspection system 1 of the third embodiment is the same as that of the inspection system 1 of the second embodiment shown in FIG. 1. The inspection system 1 of the third embodiment differs from the inspection system 1 of the second embodiment in the function. and the operation of the inspection device 50.

When the inspection device 50 is given an inspection surface of the workpiece W designated by an inspector and is given a representative inspection point for determining an inspection region from the inspector, the inspection device 50 generates an inspection path automatically. In the following description, the inspection surface of the workpiece W is assumed to be a rectangular flat surface.

Figure 9A:
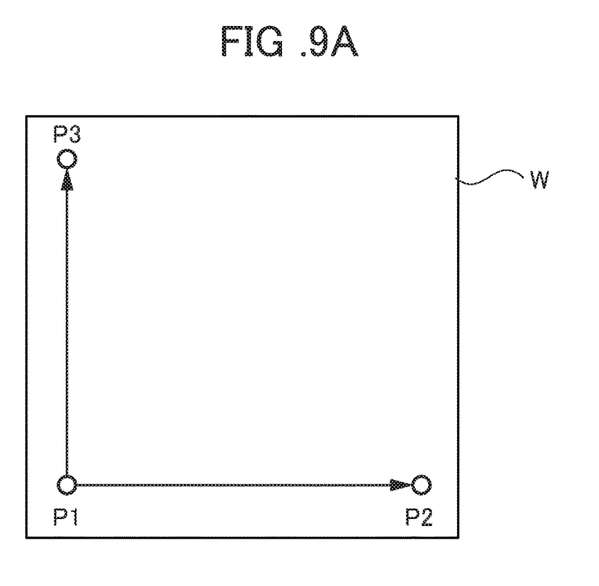
FIG. 9A is a plan view of a workpiece for explaining an example of automatic generation of an inspection path by an inspection device in an inspection system according to a third embodiment.
Figure 9B:
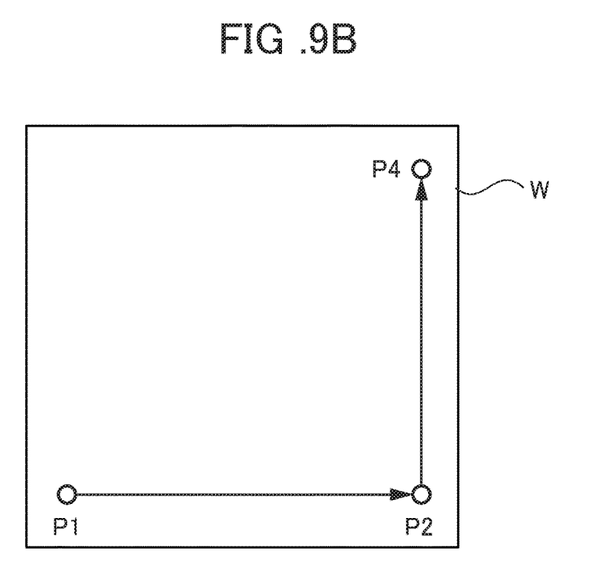
FIG. 9B is a plan view of the workpiece for explaining a different example of automatic generation of an inspection path by the inspection device in the inspection system according to the third embodiment.

FIGS. 9A, 10, 11, and 12A are plan views of the workpiece W for explaining an example of automatic generation of an inspection path. As shown in FIG. 9A, the inspection device 50 is given an inspection point P1, an inspection point P2, and an inspection point P3 at three corners of the inspection surface of the workpiece W from the inspector, and is taught the positions and the postures of the robot 30 at the inspection points P1, P2, and P3 by the inspector. As shown in FIG. 9B, the inspection device 50 may be taught the inspection points P1 and P2, and an inspection point P4.

Figure 10:
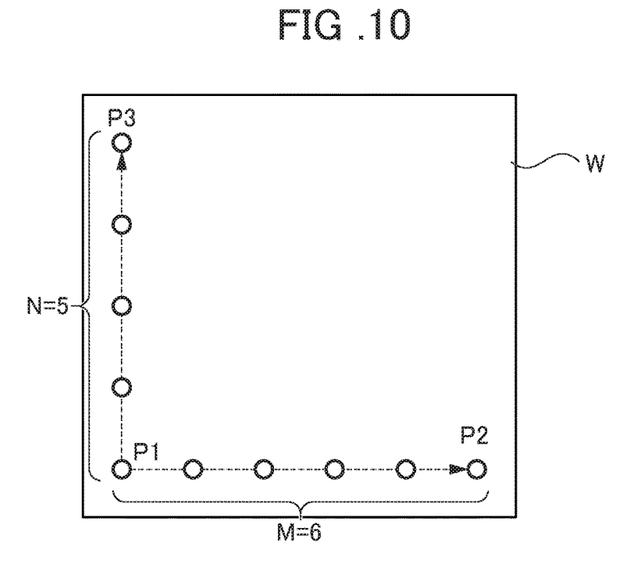
FIG. 10 is a plan view of the workpiece for explaining the example of automatic generation of the inspection path by the inspection device in the inspection system according to the third embodiment.

As shown in FIG. 10, the inspection device 50 determines an amount of movement from the inspection point P1 to the inspection. point P2 and an amount of movement from the inspection point P1 to the inspection point P3 (in FIG. 9B, an amount of movement from the inspection point P2 to the inspection point P4). The inspection device 50 divides the determined amount of movement from the inspection point P1 to the inspection point P2 by (M-1) based on an intended number P of lattice points (six, for example) to determine inspection intervals between the inspection point P1 and the inspection point P2. Likewise, the inspection device 50 divides the determined amount of movement from the inspection point P1 to the inspection point P3 by (N-1) based on an intended number N of lattice points (five, for example) to determine inspection intervals between the inspection point P1 and the inspection point P3. The intended numbers of lattice points are designated by the inspector. A parameter for inspection intervals designated by the inspector is not limited to the number of lattice points. For example, the inspector may directly designate inspection intervals in a direction from the inspection point P1 to the inspection point P2, and inspection intervals in a direction from the inspection point P1 to the inspection point P3.

Figure 11:
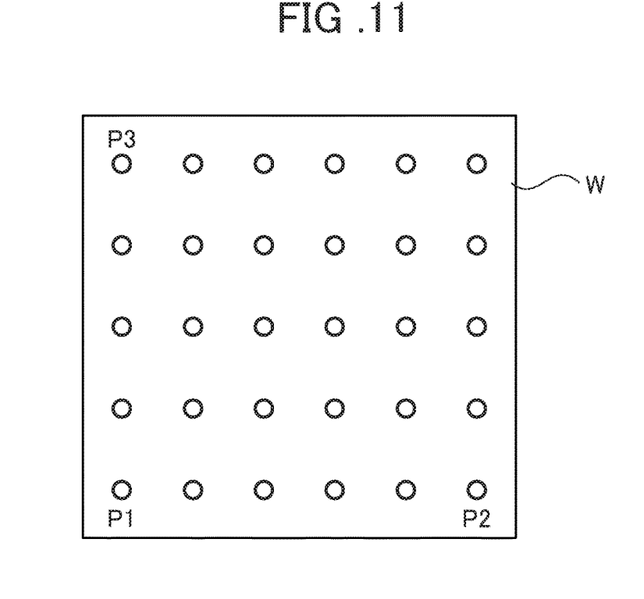
FIG. 11 is a plan view of the workpiece for explaining the example of automatic generation of the inspection path by the inspection device in the inspection system according to the third embodiment.

Next, as shown in FIG. 11, the inspection device 50 locates multiple inspection points in a lattice pattern on the inspection surface of the workpiece W based on the determined inspection intervals between the inspection point P1 and the inspection point P2 and the determined inspection intervals between the inspection point P1 and the inspection point P3.

Figure 12A:
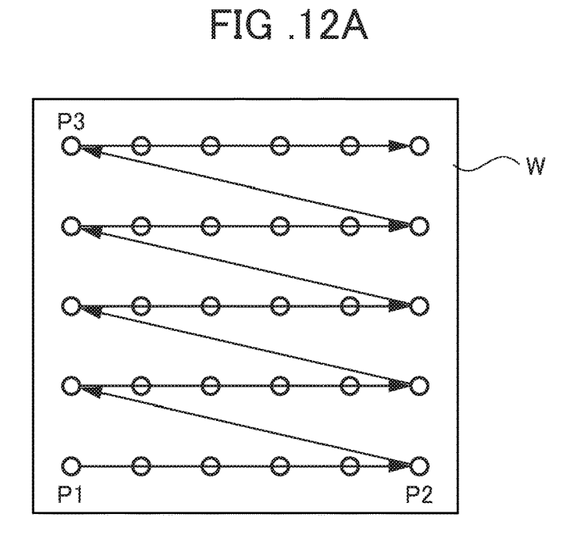
FIG. 12A is a plan view of the workpiece for explaining the example of automatic generation of the inspection path by the inspection device in the inspection system according to the third embodiment.
Figure 12B:
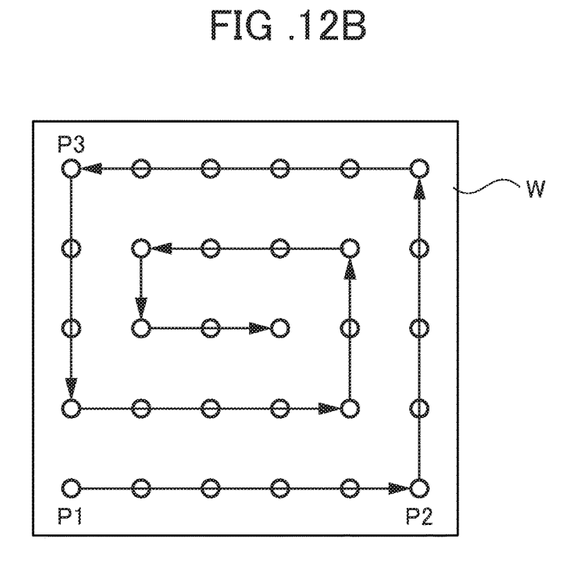
FIG. 12B is a plan view of the workpiece for explaining a different example of automatic generation of an inspection path by the inspection device in the inspection system according to the third embodiment.

Next, the inspection device 50 determines the order of passing through the inspection points, specifically, an inspection path and an inspection direction. As shown in FIG. 12A, for example, the inspection device 50 may set an inspection path and an inspection direction in such a manner that inspection proceeds along one line from one end toward the opposite end, and after the inspection along the one line is finished, inspection starts again from one end and proceeds in the same direction along a next inspection line, specifically, inspection proceeds along lines one by one in the same direction. However, this is not the only way of setting an inspection path and an inspection direction. As shown in FIG. 11B, for example, an inspection path and an inspection direction may be set in a scroll (spiral) pattern, etc.

The inspection system 1 of this embodiment is capable of achieving an effect comparable to the effect achieved by the inspection system 1 of the second embodiment.

(Modification of Third Embodiment)

Figure 13A:
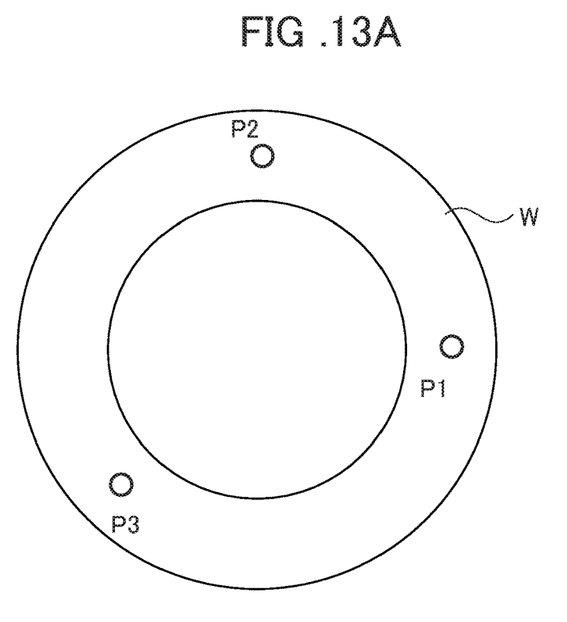
FIG. 13A is a plan view of a workpiece for explaining a different example of automatic generation of an inspection path by the inspection device in the inspection system according to the third embodiment.
Figure 13B:
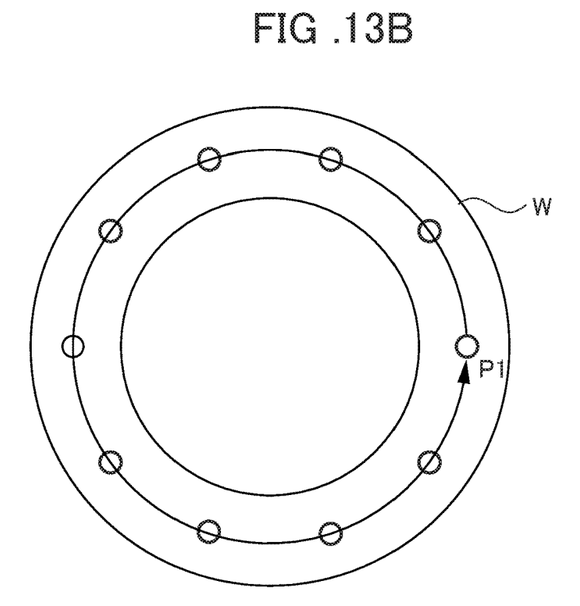
FIG. 13B is a plan view of the workpiece for explaining the different example of automatic generation of the inspection path by the inspection device in the inspection system according to the third embodiment.

The automatic generation of an inspection path of this embodiment may be applied to the shape of an inspection surface of the workpiece H having any regularity, and the shape of the inspection surface of the workpiece W is not limited to a rectangle. A shown in FIG. 13A, for example, the inspection surface of the workpiece W may have an annular (ring-like) shape. In this case, as shown in FIG. 13B, the inspection device 50 may locate multiple inspection points along a circle passing through an inspection point P1, an inspection point P2, and an inspection point P3 given by an inspector, and determine the order of passing through the inspection points starting from the inspection point P1, specifically, determine an inspection path and an inspection direction.

The present invention is not limited to the embodiments of the present invention described above. The effects described in the embodiments are merely a list of the most preferable effects resulting from the present invention. Effects achieved by the present invention are not limited to those described in the embodiments.

For example, the inspection system 1 described in the foregoing embodiments is to make inspection to determine the presence or absence of a defect (flaw, for example) on the workpiece (inspection target) W. Meanwhile, the characteristics of the present invention are applicable to various types of inspection systems that make various types of inspections on an inspection target based on an image of the inspection target captured by an image capture device such as a camera.

EXPLANATION OF REFERENCE NUMERALS 1 inspection system
10 Camera (image capture device)
20 Blower
22 Blow nozzle
30 Robot
32 Arm tip
40 Robot controller
50 Inspection device
W Work (inspection target)

What is claimed is:

1. An inspection system that makes image inspection on an inspection target, comprising:
  an image capture device that captures an image of the inspection target;
  a blower with a blow nozzle from which clean gas is blown out to the inspection target;
  a robot with an arm tip to which the image capture device and the blow nozzle, or the inspection target is attached; and
  an inspection. device that makes image inspection on the inspection target based on an image captured by the image capture device, wherein
  the inspection device generates an operation program for the robot based on the position of the image capture device and that of the blow nozzle relative to each other so as to move the blow nozzle ahead of the image capture device relative to the inspection target.

2. The inspection system according to claim 1, wherein the image capture device and the blow nozzle are attached to the arm tip of the robot, and
  the inspection device generates the operation program for the robot so as to achieve agreement between a direction from the image capture device toward the blow nozzle and an inspection. direction of an inspection path for image inspection on the inspection target.

3. The inspection system according to claim 2, wherein the inspection device sets the direction from the image capture device toward the blow nozzle as a traveling direction of the arm tip of the robot, and
  the inspection device generates the operation program for the robot so as to achieve agreement between the traveling direction of the arm tip of the robot and the inspection direction of the inspection path for image inspection on the inspection target.

4. The inspection system according to claim 1, wherein the inspection device generates the operation program for the robot based on teaching of the operation of the robot by an inspector.

5. The inspection system according to claim 1, wherein the inspection device generates the operation program for the robot automatically based on a direction from the image capture device toward the blow nozzle or a direction opposite the direction from the image capture device toward the blow nozzle, and an inspection direction of an inspection path from a current position to a next inspection point.

6. The inspection system according to claim 1, wherein the inspection. device generates an inspection path for image inspection on the inspection target automatically by setting multiple inspection points on an inspection surface of the inspection target and determining an order is which inspection is made at the multiple inspection points.

7. The inspection system according to claim 1, wherein a blowing-out direction of the clean gas from the blow nozzle is tilted to a direction from the image capture device toward the blow nozzle.

8. The inspection system according to claim 7, wherein the blowing-out direction of the clean gas from the blow nozzle is further tilted to a direction intersecting the direction from the image capture device toward the blow nozzle.

* * * * *